(12) United States Patent
Nagasawa

(10) Patent No.: US 6,632,015 B2
(45) Date of Patent: Oct. 14, 2003

(54) THERMAL ANALYSIS APPARATUS

(75) Inventor: Jun Nagasawa, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/837,835

(22) Filed: Apr. 18, 2001

(65) Prior Publication Data

US 2001/0038660 A1 Nov. 8, 2001

(30) Foreign Application Priority Data

Apr. 26, 2000 (JP) ........................................ 2000-125442

(51) Int. Cl.$^7$ .............................................. G01N 25/20
(52) U.S. Cl. ........................................... 374/11; 374/33
(58) Field of Search .............................. 374/11, 10, 34, 374/33, 31

(56) References Cited

U.S. PATENT DOCUMENTS

| | | | | |
|---|---|---|---|---|
| 5,547,282 A | * | 8/1996 | Pinhack et al. | 374/34 |
| 5,549,387 A | * | 8/1996 | Schawe et al. | 374/10 |
| 5,599,104 A | * | 2/1997 | Nakamura et al. | 374/11 |
| 5,711,604 A | * | 1/1998 | Nakamura | 374/10 |
| 5,813,763 A | * | 9/1998 | Plotnikov et al. | 374/11 |
| 5,967,659 A | * | 10/1999 | Plotnikov et al. | 374/11 |
| 6,146,012 A | * | 11/2000 | Nakamura et al. | 374/11 |
| 6,170,984 B1 | * | 1/2001 | Schawe et al. | 374/10 |

* cited by examiner

Primary Examiner—Diego Gutierrez
Assistant Examiner—Stanley J. Pruchnic, Jr.
(74) Attorney, Agent, or Firm—Adams & Wilks

(57) ABSTRACT

With input compensation-type differential scanning calorimeters of the related art, the power supplied fluctuated even with non-endothermic reference materials, and the reference material side temperature therefore also fluctuated. Mutual interference between feedback loops also made precise temperature control difficult. In the present invention, power supplied to the sample side is changed to compensate for a temperature difference between the sample side and the reference material side using a differential thermal feedback loop, power to be supplied to the reference material side heater to make the reference material side temperature correspond to the program temperature is controlled, and the same amount of the power is also supplied to the sample side with the average temperature feedback loop. Further, in the present invention, the power supplied to heat reservoir the sample side is changed to compensate for a temperature difference between the sample side and the reference material side using a differential thermal feedback loop, and the average temperature feedback loop controls the heat reservoir surrounding the sample and the reference material to make it correspond to the program temperature.

12 Claims, 3 Drawing Sheets

THERMAL ANALYSIS APPARATUS

BACKGROUND OF THE INVENTION

The present invention relates to thermal analysis apparatus for measuring changes of physical or chemical characteristics of a sample according to the temperature.

More particularly, the present invention relates to a differential scanning calorimeter for performing analysis by measuring endothermic/exothermic heat accompanying transitions, etc., of a sample as a function of temperature.

With respect to the above differential scanning calorimeters, two kinds such as the heat flux-type and the power compensation-type calorimeters differentiated by the measurement method are well known. The power compensation-type calorimeter is also referred to herein as an input compensation-type calorimeter.

A basic structure for a power compensation-type differential scanning calorimeter is shown in FIG. 3.

Numerals 28 and 29 are holders for mounting a sample and a reference material, and temperature sensors 30, 31 composed of a resistor for temperature detection, etc and heaters 32, 33 for heat flow feedback are provided for each holder.

The thermal signal of each temperature sensor is measured with a temperature measuring instrument 34, the average temperature of the sample side and the reference material side is output to an average temperature controller 35, and the differential temperature is output to a differential thermal controller 36.

In the DSC of this type, control and measurement are performed by two feedback loop systems.

The first feedback loop is for the average temperature, which compares the average temperature between the sample side and the reference material side to the program temperature outputted by the program temperature generator, outputs the power to the heater for heat flow feedback to make both correspond to each other, and then makes changes to both holders according to the temperature program.

The second feedback loop is for differential temperature, and outputs the appropriate power to the sample side heater 32 and the reference material side heater 33 to set the differential temperature outputted by the temperature sensor back to zero.

Specifically, it adjusts the distribution of the power to heat each heater according to the temperature differential while maintaining a constant total amount of power supplied to the sample side heater 32 and the reference material side heater 33, and exerts control to set the temperature differential back to zero.

As a result, when the endothermic phenomenon occurs at the sample side, the power to be supplied to the sample side heater 32 is increased, and the power to be supplied to the reference material side heater 33 is decreased by the same amount.

This power difference is outputted as a sample endothermic/exothermic signal (DSC signal).

For this type of invention of the related art as disclosed in Japanese Patent publication Hei.11-160261, a structure, which comprises a detector constituted by a temperature sensor and a heater for heat flow feedback, where the detector provided inside a heat sink, and performs DSC output using a control loop similar to the above while controlling the heat sink temperature, is already known.

However, with the input compensation-type differential scanning calorimeters of the related art, the distribution of power to be supplied to the sample side and the reference material side is adjusted according to the temperature difference to compensate for the temperature difference between the sample side and reference material side caused by the differential thermal feedback loop. As the amount of power supplied fluctuates even with a non-endothermic reference material, there is therefore a problem that the reference material side temperature also fluctuates.

Moreover, in this type of the input compensation-type differential scanning calorimeter of the related art, power is supplied to both the sample side and the reference material side by the double feedback loops. This causes mutual interference, so that the output of one of the feedback loops influences the other feedback loop, making precise temperature control difficult.

It is the object of the present invention to provide thermal analysis apparatus which resolves the above problems.

SUMMARY OF THE INVENTION

To resolve the above problems, a first differential scanning calorimeter relating to the present invention comprises a sample holder for mounting a sample container containing a sample, a sample temperature sensor for measuring the sample temperature, a sample side heater to heat the sample, a reference material holder for mounting the reference material container containing the reference material, a reference material temperature sensor for measuring the reference material temperature, a reference material side heater to heat the reference material, a temperature measuring instrument for measuring the reference material side temperature and the differential temperature between the sample side and the reference material side, a program temperature generator; a reference material side temperature controller for outputting the power to the sample side heater and the reference material side heater based on the result obtained by comparing the reference material side temperature outputted by the reference material temperature measuring instrument to the desired value of the temperature outputted by the program temperature generator, and a differential thermal compensator for inputting the differential temperature outputted by the temperature measuring instrument and outputting the power to the sample side heater to set the value back to zero.

A second differential scanning calorimeter relating to the present invention comprises a sample holder for mounting a sample container containing a sample, a sample temperature sensor for measuring the sample temperature, a sample side heater for heating the sample, a reference material holder for mounting the reference material container containing the reference material, a reference material temperature sensor for measuring the reference material temperature, a reference material side heater to heat the reference material, a temperature measuring instrument for measuring the differential temperature between the sample side and the reference material side, a differential thermal compensator for taking as input the differential temperature outputted by the temperature measuring instrument and outputting the power to the sample side heater to set the value back to zero, a bias power output instrument for outputting the fixed bias power to the sample side heater and the reference material side heater, a heat reservoir surrounding the sample holder and the reference material holder, a heat reservoir temperature measuring instrument for measuring the heat reservoir temperature, a program temperature generator, and a heat reservoir temperature controller for controlling the heat reservoir to make the heat reservoir temperature correspond to the desired value of temperature outputted by the program temperature generator.

With the first configuration, the reference material temperature controller outputs the power to the reference material side heater so that the reference material temperature and the program temperature correspond to each other.

The same amount of power is outputted to the sample side heater and both holders are adjusted according to the temperature program.

When a temperature difference occurs between the sample and the reference material, the differential thermal compensator outputs power to the sample side to set the value back to zero, and detects the power outputted by the differential thermal compensator as the sample endothermic/exothermic signal (DSC signal).

The second configuration brings the effect that the heat reservoir controller controls the heat reservoir to make the heat reservoir temperature and the program temperature correspond to each other.

When a temperature difference occurs between the sample and the reference material, the differential thermal compensator outputs power to the sample side to set the value back to zero, and detects the power outputted by the differential thermal compensator as the sample endothermic/exothermic signal (DSC signal).

As a result, the power to be supplied to the reference material side does not fluctuate due to the endothermic/exothermic phenomena of the sample, so that the reference material side temperature does not fluctuate.

Additionally, the places to be supplied with power can be separated with the two feedback loops, so that the mutual interference between the two feedback loops is prevented and precise temperature control is possible.

DETAILED DESCRIPTION OF THE PREFERRED EMBODIMENT

[First Embodiment]

An embodiment of the present invention will be described in the following based on the drawings.

Figure 1:
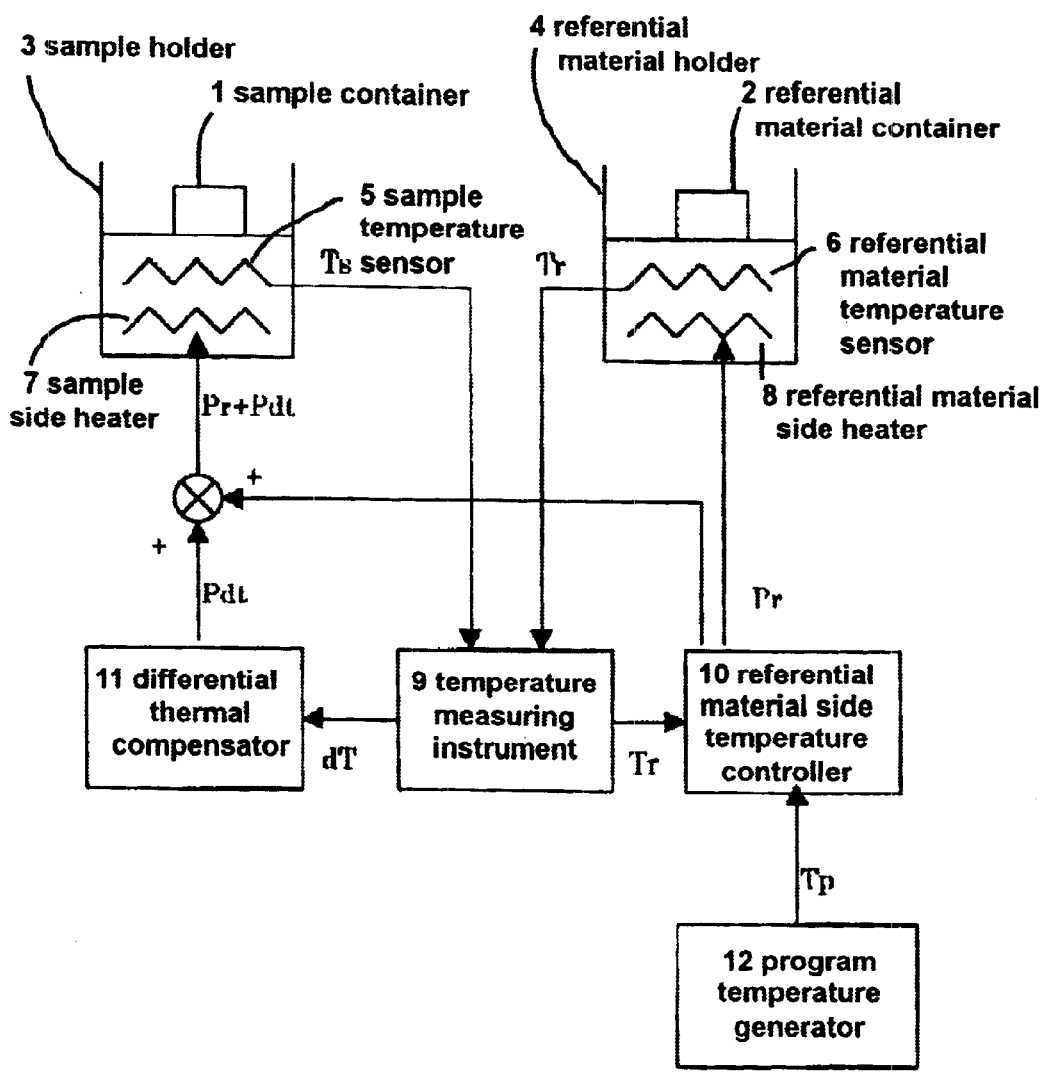
FIG. 1 is an explanatory drawing of a first embodiment of the present invention.

FIG. 1 shows a first embodiment of the present invention. A sample container 1 contains a sample to be measured with the thermal analysis apparatus.

A reference material container 2 contains a reference material.

Holders 3 and 4 are for mounting the sample container 1 and the reference material container 2.

A sample temperature sensor 5 and a reference material temperature sensor 6 composed of the resistor for temperature detection, etc and a sample heater 7 and a reference material heater 8 are arranged in proximity to each holder.

A temperature measuring instrument 9 is connected to the sample temperature sensor 5 and the reference material temperature sensor 6, and measures the thermal signal from both sensors.

A reference material temperature controller 10 is connected to the temperature measuring instrument 9 and a program temperature generator 12, and controls power Pr to be outputted to the sample heater 7 and the reference material heater 8.

A differential thermal compensator 11 is connected to a temperature measuring instrument 9, and controls the power Pdt to be outputted to the sample heater 7.

Next, the operation of the apparatus shown in FIG. 1 is described.

First, a measurer places the sample container 1 containing the sample to be measured and the reference material container 2 containing the reference material of which the thermal stability in the temperature range to operate the measurement is verified on each holder.

Then the measurer inputs the temperature program into the program temperature generator 12, and gives instructions to start measurements.

When the measurement is started, the program temperature generator 12 outputs the program temperature Tp to the reference material temperature controller 10 according to the temperature program.

The temperature measuring instrument 9 measures the thermal signal inputted from the sample temperature sensor 5 and the reference material temperature sensor 6 as the sample temperature Ts and the reference material temperature Tr, outputs the reference material temperature Tr to the reference material temperature controller 10, and outputs the differential temperature dT between the sample temperature Ts and the reference material temperature Tr to the differential thermal compensator 11.

The reference material temperature controller 10 compares the program temperature Tp with the reference material temperature Tr, and outputs the appropriate power Pr to the reference material heater 8 to make both correspond to each other, as well as outputting the same amount of power to the sample heater 7.

A series configuration comprising the reference material temperature sensor 6, the sample heater 7, the reference material heater 8, the temperature measuring instrument 9, the reference material temperature controller 10, and the program temperature generator 12 forms the first feedback loop.

This first feedback loop functions so as to make changes to both holders according to the temperature program by outputting the power Pr to the reference material heater 8 to make the reference material temperature Tr and the program temperature Tp correspond to each other, and by outputting the same amount of power to the sample side heater.

The differential thermal compensator 11 outputs the appropriate power Pdt to the sample heater 7 to set the differential temperature dT back to zero, and exerts control to increase power upon the occurrence of the endothermic phenomenon at the sample side, and to decrease power upon the occurrence of the exothermal phenomenon.

A series configuration comprising the sample temperature sensor 5, the reference material temperature sensor 6, the sample heater 7, the temperature measuring instrument 9, and the differential thermal compensator 11 forms the second feedback loop.

This feedback loop functions so as to set the temperature difference back to zero by adjusting the power Pdt to be outputted to the sample heater 7 according to the temperature difference between the sample side and the reference material side, and outputs power Pdt outputted by the differential thermal compensator as the sample endothermic/exothermic signal (DSC signal).

[Second Embodiment]

Figure 2:
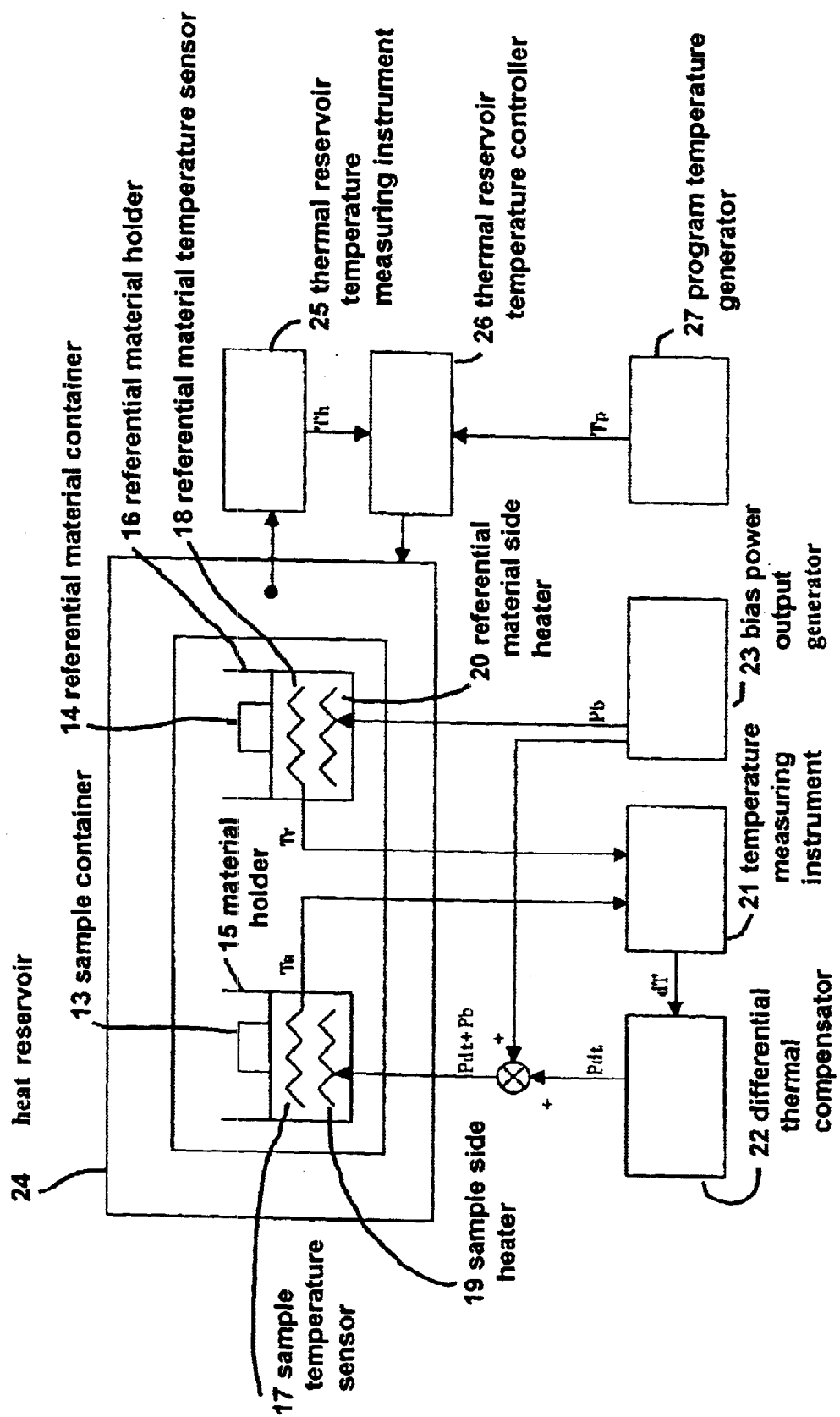
FIG. 2 is an explanatory drawing of a second embodiment of the present invention.
Figure 3:
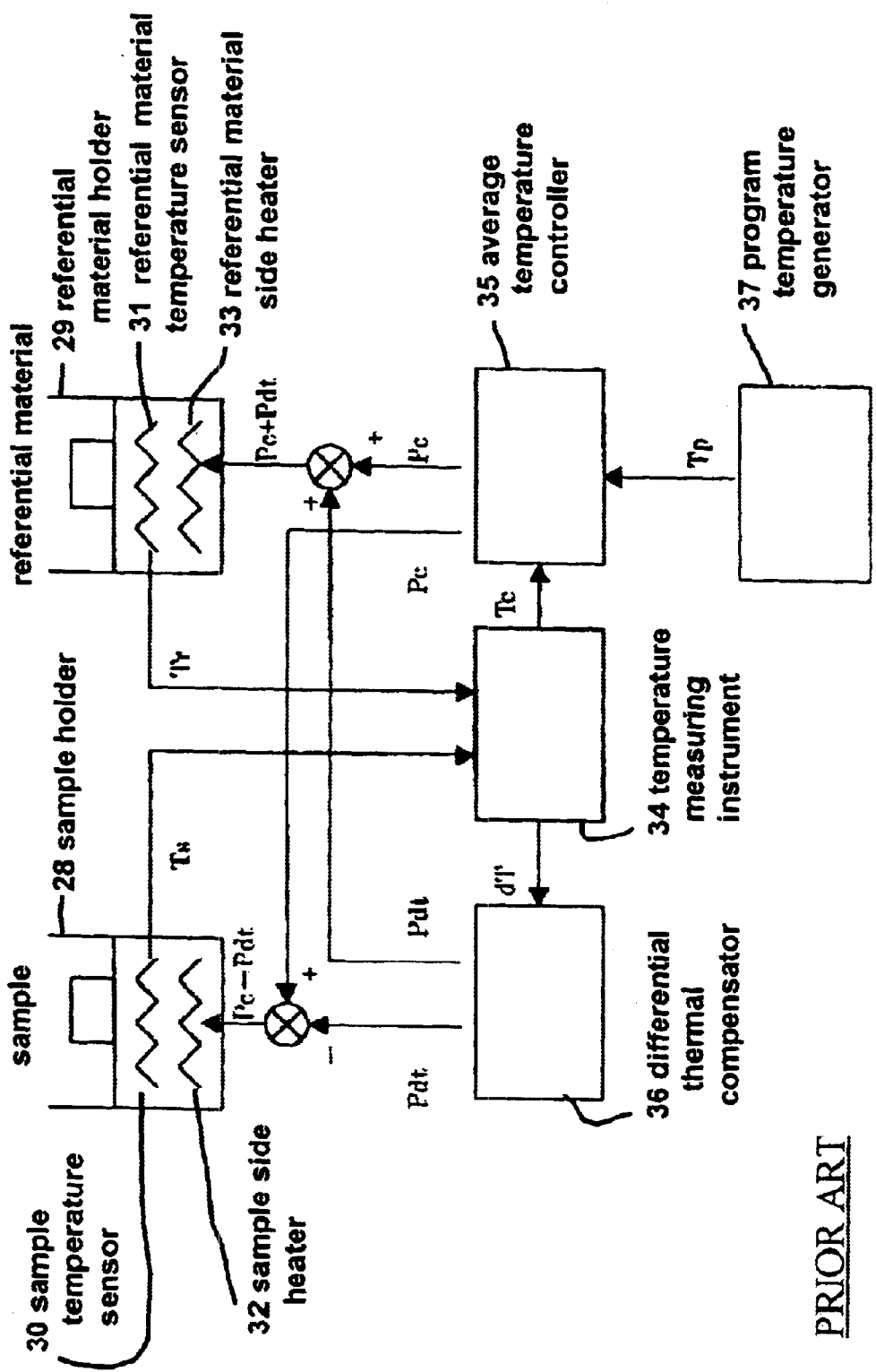
FIG. 3 is an explanatory drawing of the basic structure of the input compensation-type differential scanning calorimeter of related art.

FIG. 2 shows a second embodiment of the present invention.

A sample container 13 contains a sample to be measured with the thermal analysis apparatus.

A reference material container 14 contains a reference material.

Holders 15 and 16 are for mounting the sample container 13 and the reference material container 14.

A sample temperature sensor 17 and a reference material temperature sensor 18 composed of a resistor for temperature detection, etc., a sample heater 19 and a reference material heater 20 are arranged in proximity to each holder.

A temperature measuring instrument 21 is connected to the sample temperature sensor 17 and the reference material temperature sensor 18, and measures the thermal signal from both sensors.

A bias power output generator 23 outputs a fixed bias power to the sample side heater 19 and the reference material side heater 20. The value of the fixed bias power Pb can be modified using settings.

A differential thermal compensator 22 is connected to a temperature measuring instrument 21, and controls the power Pdt to be outputted to the sample heater 19.

A heat reservoir (or heat sink) 24 surrounds the sample holder and the reference material holder.

A heat reservoir temperature measuring instrument measures the temperature Th of the heat reservoir 24, and outputs this to a heat reservoir temperature controller 26. The heat reservoir temperature controller 26 is connected to the heat reservoir temperature measuring instrument 25 and the program temperature generator 27, and controls the temperature of the heat reservoir 24.

Next, the operation of the apparatus shown in FIG. 2 is described.

First, a measurer places the sample container 13 containing the sample to be measured and the reference material container 14 containing the reference material of which the thermal stability in the temperature range to operate the measurement is verified on each holder.

Then the measurer inputs the temperature program into the program temperature generator 27, and gives an instruction to start measurement.

When the measurement is started, the program temperature generator 27 outputs the program temperature Tp to the heat reservoir temperature controller 26 according to the inputted temperature program.

The heat reservoir temperature controller 26 compares the program temperature Tp with the heat reservoir temperature Th inputted from the heat reservoir temperature measuring instrument 25, and exerts control to make both correspond to each other.

A series configuration comprising the heat reservoir 24, a heat reservoir temperature measuring instrument 25, a thermal reservoir controller 26, and a program temperature generator 27 forms the first feedback loop.

This makes the heat reservoir 24 temperature correspond to the program temperature Tp.

When the heat reservoir 24 is heated, the heat is conducted to the sample container 13 and the reference material container 14. As a result, the sample container 13 and the reference material container 14 is controlled according to the program temperature Tp.

A temperature measuring instrument 21 measures the thermal signals from the sample temperature sensor 17 and the reference material temperature sensor 18 as the sample temperature Ts and the reference material temperature Tr, and outputs the differential temperature dT between the sample temperature Ts and the reference material temperature Tr to a differential thermal compensator 22.

A differential thermal compensator 22 outputs the appropriate power Pdt determined from the differential temperature dT input from the temperature measuring instrument 21 to the sample side heater to set the differential temperature dT back to zero.

This control increases the power at the occurrence of the endothermic phenomenon at the sample side, and decreases the power upon the occurrence of an exothermal phenomenon. A series configuration comprising the sample temperature sensor 17, the reference material temperature sensor 18, the sample heater 19, the reference material heater 20, the temperature measuring instrument 21, and the differential thermal compensator 22 forms the second feedback loop.

The function here is to set the temperature difference back to zero by adjusting the power outputted to the sample heater 19 according to the temperature difference between the sample side and the reference material side.

This outputs the power Pdt outputted by the differential thermal compensator 22 as the sample endothermic/exothermic signal (DSC signal).

Here, the shape of the sample holder does not matter providing the shape is capable of mounting the sample container, and the temperature sensor and the sample heater are arranged in proximity to it.

Also, it is needless to say that the temperature measuring instruments 9, 21, the differential thermal compensator 11, 22, the reference material temperature controller 10, the program temperature generator 12, 27, the bias power generator 23, the heat reservoir temperature measuring instrument 25, and the heat reservoir temperature controller 26 shown in this embodiment can be configured with the analog circuit, the digital circuit, or a combination of both.

According to the present invention, the fluctuation of the reference material side temperature can be prevented only by changing the amount of power supplied to the sample side with the differential thermal feedback loop to compensate for the temperature difference occurring between the sample side and the reference material side.

Additionally, the places to be supplied with power can be separated with two feedback loops, so that mutual interference between the two feedback loops is prevented and precise temperature control is enabled.

What is claimed is:

1. A thermal analyzer comprising: a sample holder for holding a sample; a reference material holder for holding a reference material; a temperature measuring device for measuring temperatures of the reference material and the sample; a program temperature generator for outputting a temperature value according to a stored program; a first feedback loop for controlling temperatures inside the sample holder and the reference material holder by comparing a temperature output by the temperature measuring device with a desired temperature value output by the program temperature generator; and a second feedback loop comprised of a differential thermal compensator for controlling the temperature inside the sample holder according to a differential temperature between the sample and the reference material, so that only the first feedback loop outputs a signal for controlling the reference material temperature; wherein power output by the differential thermal compensator is detected as a sample endothermic/exothermic signal.

2. A thermal analyzer according to claim 1; further comprising a sample temperature sensor arranged proximate the sample holder for measuring the sample temperature, a sample heater arranged proximate the sample holder for heating the sample, a reference material temperature sensor arranged proximate the reference material holder for measuring the reference material temperature, and a reference material heater arranged proximate the reference material holder for heating the reference material; and wherein the first feedback loop comprises a heat reservoir surrounding the sample holder and the reference material holder, a heat reservoir temperature measuring instrument for measuring heat reservoir temperature, and a heat reservoir temperature controller connected to the program temperature generator and the heat reservoir temperature measuring instrument for controlling the heat reservoir to make the heat reservoir temperature correspond to the desired value of temperature output by the program temperature generator, and the differential thermal compensator outputs power to the sample heater to set the differential temperature value to zero.

3. A thermal analyzer according to claim 1; wherein the thermal analyzer is a power compensation-type differential scanning calorimeter.

4. A power compensation-type differential scanning calorimeter comprising:

a sample holder for holding a sample container containing a sample;

a sample temperature sensor arranged proximate the sample holder for measuring the sample temperature;

a sample side heater arranged proximate the sample holder for heating the sample;

a reference material holder for holding a reference material container containing a reference material;

a reference material temperature sensor arranged proximate the reference material holder for measuring the reference material temperature;

a reference material side heater arranged proximate the reference material holder for heating the reference material;

a temperature measuring instrument connected to the sample temperature sensor and the reference material sensor for measuring the differential temperature between the sample side and the reference material side;

a program temperature generator;

a differential thermal compensator for inputting the differential temperature output by the temperature measuring instrument and outputting power to only the sample side heater effective to reduce the differential temperature value;

a bias power output generator for outputting a fixed bias power to the sample side heater and the reference material side heater;

a heat reservoir surrounding the sample holder and the reference material holder;

a heat reservoir temperature measuring instrument for measuring heat reservoir temperature; and a heat reservoir temperature controller connected to the program temperature generator and the heat reservoir temperature measuring instrument for controlling the heat reservoir to make the heat reservoir temperature correspond to the desired value of temperature output by the program temperature generator;

wherein the power output by the differential thermal compensator is detected as a sample endothermic/exothermic signal.

5. A thermal analyzer comprising: a sample holder for holding a sample; a reference material holder for holding a reference material; a plurality of heaters for heating the sample and the reference material; a program temperature generator for outputting a signal for controlling at least one of the heaters according to a pre-stored temperature program; a first feedback loop for measuring temperatures of the sample and the reference material, determining a differential temperature between the sample and the reference material, and controlling only a sample heater to reduce the differential temperature; a second feedback loop for measuring a temperature of at least one of the sample and the reference material, determining a difference between the measured temperature and a desired temperature as defined by the program temperature generator, and controlling a heater so as to reduce the difference.

6. A thermal analyzer according to claim 5; wherein the thermal analyzer is a power compensation-type differential scanning calorimeter.

7. A thermal analyzer according to claim 6; wherein the plurality of heaters comprises a sample heater proximate the sample, a reference material heater proximate the reference material, and a heat sink surrounding the sample holder and the reference material holder for simultaneously heating the sample and the reference material.

8. A thermal analyzer according to claim 7; wherein the first feedback loop comprises a temperature measuring instrument for measuring the temperature of the reference material and determining the differential temperature, and a differential thermal compensator for controlling the temperature of the sample holder according to the differential temperature.

9. A thermal analyzer according to claim 8; wherein the second feedback loop comprises a heat sink temperature measuring instrument for measuring a temperature of the heat sink, and a heat sink temperature controller connected to the program temperature generator and the heat sink temperature measuring instrument for controlling the temperature of the heat sink to correspond to a desired temperature indicated by an output signal of the program temperature generator.

10. A thermal analyzer according to claim 5; wherein the plurality of heaters comprises a sample heater proximate the sample, a reference material heater proximate the reference material, and a heat sink surrounding the sample holder and the reference material holder for simultaneously heating the sample and the reference material.

11. A thermal analyzer according to claim 5; wherein the first feedback loop comprises a temperature measuring instrument for measuring the temperature of the reference material and determining the differential temperature, and a differential thermal compensator for controlling the temperature of the sample holder according to the differential temperature.

12. A thermal analyzer according to claim 5; wherein the second feedback loop comprises a heat sink temperature measuring instrument for measuring a temperature of the heat sink, and a heat sink temperature controller connected to the program temperature generator and the heat sink temperature measuring instrument for controlling the temperature of the heat sink to correspond to a desired temperature indicated by an output signal of the program temperature generator.

* * * * *